(12) United States Patent
Kluczynski et al.

(10) Patent No.: US 7,864,323 B2
(45) Date of Patent: Jan. 4, 2011

(54) METHOD FOR MEASURING THE CONCENTRATION OF A GAS COMPONENT IN A MEASURING GAS

(75) Inventors: Pawel Kluczynski, Västra Frölunda (SE); Stefan Lundqvist, Askim (SE)

(73) Assignee: Siemens Aktiengesellschaft, Munich (DE)

( * ) Notice: Subject to any disclaimer, the term of this patent is extended or adjusted under 35 U.S.C. 154(b) by 229 days.

(21) Appl. No.: 12/156,596

(22) Filed: Jun. 2, 2008

(65) Prior Publication Data

US 2008/0304066 A1  Dec. 11, 2008

(30) Foreign Application Priority Data

Jun. 6, 2007  (EP)  ................... 07011165

(51) Int. Cl.
*G01N 21/35*  (2006.01)

(52) U.S. Cl. .................. 356/439; 250/339.13

(58) Field of Classification Search ............... 356/433, 356/436–437; 250/339.12, 339.13
See application file for complete search history.

(56) References Cited

U.S. PATENT DOCUMENTS

| | | | |
|---|---|---|---|
| 4,410,273 A | 10/1983 | Mantz et al. | |
| 5,026,991 A | 6/1991 | Goldstein et al. | |
| 5,047,639 A * | 9/1991 | Wong | 250/341.1 |
| 5,173,749 A | 12/1992 | Tell et al. | |
| 5,459,574 A | 10/1995 | Lee et al. | |
| 5,486,699 A * | 1/1996 | Fabinski et al. | 250/345 |
| 6,353,225 B1 | 3/2002 | Strzoda et al. | |
| 6,452,182 B1 * | 9/2002 | Zochbauer et al. | 250/344 |
| 7,116,422 B2 | 10/2006 | Larking et al. | |
| 2002/0084408 A1 * | 7/2002 | Shiokawa et al. | 250/281 |

OTHER PUBLICATIONS

Gurlit et al., "Lightweight diode laser spectrometer CHILD (Compact High-altitude In-situ Laser Diode) for balloon borne measurements of water vapor and methane", Applied Optics, Jan. 2005, pp. 91-102, vol. 44, Issue 1.

Durry et al., "Atmospheric $CH_4$ and $H_2$) monitoring with near-infrared inGaAs laser diodes by the SDLA, a balloonborne spectrometer for tropospheric and stratospheric in situ measurements", Applied Optics, Dec. 20, 1999, pp. 7342-7354, vol. 38, No. 36.

(Continued)

*Primary Examiner*—Gregory J Toatley
*Assistant Examiner*—Rebecca C Slomski

(57) ABSTRACT

There is described a method for measuring a concentration of a gas component in a measuring gas, wherein the light of a wavelength tunable light source is passed along a single optical path through a measuring volume containing the measuring gas and a reference cell containing a reference gas to a detector. The reference cell is selected to contain a selected isotope of the gas component to be measured in a known abundance ratio higher than the known natural-abundance isotope ratio of the gas component in the measuring volume; the light source is tuned to sweep the wavelength of the light over the absorption lines of the selected isotope and the remaining gas component; and the concentration of the gas component in the measuring volume is calculated from the ratio of the detector signals at the peaks of the absorption lines, based on Lambert's law and taking into account the known abundance isotope ratios.

5 Claims, 2 Drawing Sheets

OTHER PUBLICATIONS

Scott et al., Airborne Laser Infrared Absorption Spectrometer (ALIAS-II) for insitu atmospheric measurements of $N_2O$, $CH_4$, CO, HCL and $NO_2$ from balloon or remotely piloted aircraft platforms, Applied Optics, Jul. 20, 1999, pp. 4609-4622, vol. 38, No. 21.

* cited by examiner $^{16}O_2$, R11R11
13148.136 cm$^{-1}$ $^{18}O_2$, R11R11
13148.688 cm$^{-1}$ line m line i

METHOD FOR MEASURING THE CONCENTRATION OF A GAS COMPONENT IN A MEASURING GAS

CROSS REFERENCE TO RELATED APPLICATIONS

This application claims priority of European Patent Office application No. 07011165.3 EP filed Jun. 6, 2007, which is incorporated by reference herein in its entirety.

FIELD OF INVENTION

The invention relates to a method for measuring the concentration of a gas component in a measuring gas, wherein the light of a wavelength tunable light source is passed along a single optical path through a measuring volume containing the measuring gas and a reference cell containing a reference gas to a detector for generating a signal indicative of the wavelength dependent absorption of the light, and wherein the reference gas comprises the gas component in a known concentration.

BACKGROUND OF INVENTION

Such a method is known from U.S. Pat. No. 6,353,225.

In spectroscopic gas detection, the concentration of a known gas component in a gas mixture (measuring gas) is determined from a measured wavelength-specific absorption of the gas component. For this purpose, the measuring gas is introduced in a measuring volume having a predetermined optical path length, e.g. a sample cell or, in case of in-situ process measurements, a gas-leading pipe, furnace, funnel or the like. The light of a tunable light source, such as a diode laser, is transmitted through the measuring volume to a detector for generating a signal dependent on the wavelength-selective light absorption in the optical path of the measuring volume.

The gas mixture in which the measurement is performed is generally not well known and the gas component of interest must be measured with minimum interference from this background. It is therefore important to maintain an accurate lock to the absorption line of said gas component. This can be done by incorporating a reference cell which encloses the gas component of interest or another suitable gas component of constant concentration. This cell can be placed in an optical reference path which is split off from the main optical path through the measuring volume or it can be placed in the main optical path in-line with the measuring volume.

U.S. Pat. Nos. 4,410,273, 5,026,991, 5,173,749 and 5,459,574 show several variants of an absorption spectroscopy system, all using a beam splitter or an optical fiber coupler. The beam splitter and coupler invariably contribute to the noise of the system due to etalon effects. U.S. Pat. No. 5,459,574 further discloses an off-line locked spectroscopy system wherein the reference cell contains a reference gas having an absorption wavelength differing from that of the gas component of interest in the measuring volume by a predetermined amount. The purpose of this is to solve the problem that certain gases cannot be contained in a reference cell since they will react with or corrode the cell. The wavelength of the light source is locked to the absorption wavelength of the reference gas and then by means of a controller displaced by said predetermined amount to the absorption wavelength of the gas component to be measured. The precision of this offset is, however, depending on the precision of the electronic controller and can be subject to instabilities and temperature drift. Moreover, the light can accidentally be offset so that the optical emission wavelength coincides with that of an interfering gas in the gas mixture in the measurement volume.

The initially mentioned U.S. Pat. No. 6,353,225 shows an absorption spectroscopy system comprising a reference cell placed in the main optical path in-line with the measuring volume. The reference cell contains a sufficient amount of the gas component to be measured so that permanent preabsorption takes place. The gas concentration to be measured is obtained from the growth of the absorption. Alternatively to the reference gas containing a portion of the gas component to be measured, a neighboring atmospheric line of $H_2O$ or $CO_2$, for example, can be used as a wavelength reference; however, if measurements are performed in an unknown gas mixture it is quite likely that these gases will be found and that their absorption will add to that of the reference gas in an unknown way.

The intensity of the light impinging onto the detector depends on both the wavelength-specific absorption by the gases in the optical path and the wavelength-independent total optical transmission including optical losses in the measuring system and the measurement path. Thus, normalization of the signal of the detector is necessary.

The most straight forward method to measure the non-gas related transmission is to use a direct detection. The wavelength of the light is swept by a triangular or sawtooth waveform over the absorption line of the gas component to be measured. The peak of the received triangularly or sawtooth shaped optical signal, which is well separated from the absorption peak, is compared with the signal from a monitor detector which directly monitors the output intensity of the light source. [Applied Optics, Vol. 38, Issue 36, pp. 7342-7354 (December 1999) and Applied Optics, Vol. 44, Issue 1, pp. 91-102 (January 2005)]. In wavelength modulation spectroscopy (WMS) a combination of wavelength modulation and direct detection can be used [Applied Optics, Vol. 38, Issue 21, pp. 4609-4622 (July 1999)]. These techniques are mostly developed for atmospheric monitoring; in order to be used in harsh industrial environment, the modulation rate has to be increased in order to place the signal energy above that of the turbulent measuring medium.

In wavelength modulation spectroscopy (WMS) an indirect measure of the non-gas related optical transmission can be obtained by the use of the wavelength modulation signal [U.S. Pat. No. 5,173,749], which makes it necessary to introduce a separate detection chain for the fundamental frequency. An intentionally injected pilot tone at a higher harmonic of said wavelength modulation signal [U.S. Pat. No. 7,116,422] avoids the use of a separate electronic channel.

SUMMARY OF INVENTION

The invention seeks to provide a simple method for measuring the concentration of a gas component in a measuring gas.

According to the invention this can be achieved for the method defined of the type mentioned initially in that the gas component in the reference cell is selected to contain a selected isotope in a known abundance ratio higher than the known natural-abundance isotope ratio of the gas component in the measuring volume, the light source is tuned to sweep the wavelength of the light over the absorption lines of the selected isotope and the remaining gas component, and the concentration of the gas component in the measuring volume is calculated from the ratio of the detector signals at the peaks of the absorption lines, based on Lambert's law and taking into account the known abundance isotope ratios.

Forming the ratio of the detector signals advantageously eliminates the non-gas related optical transmission, thus making an independent normalization scheme no longer necessary.

Preferably the wavelength of the tunable light source is locked to the absorption line of the selected isotope. Due to the difference in molecular masses between the different isotopes of the same gas, the frequency spectra will be shifted. The shift is well defined and depends on the masses of the different isotopes and the type of molecular transition. This phenomenon provides a well defined off-line lock to the measured absorption gas peak. The reason for this off-line lock is to avoid a permanent preabsorption that decreases the sensitivity especially when measuring very low concentration levels. The use of an isotope line guarantees that there will be a line suitably offset from the line we are measuring on. There have been disclosed systems that have relied on the fortuitous near coincidence between the absorption line of the gas component to be measured and another gas absorption line to provide an off-line center lock. For several gases such as oxygen no such suitable gas can be found that provides a line suitable for off-line locking. The relations between the line strength of different isotope lines are well known so that the isotope reference peak can be moreover used as a concentration normal.

In the method according to the invention, for measuring the concentration of oxygen the O-18 isotope is used as the selected isotope in the reference cell and the detector signals obtained at the peaks of the absorption lines of the O-18 and O-16 isotopes are used for calculating oxygen concentration.

BRIEF DESCRIPTION OF THE DRAWINGS

The present invention will be now described, by way of example, with reference to the accompanying drawings, in which.

DETAILED DESCRIPTION OF INVENTION

Figure 1:
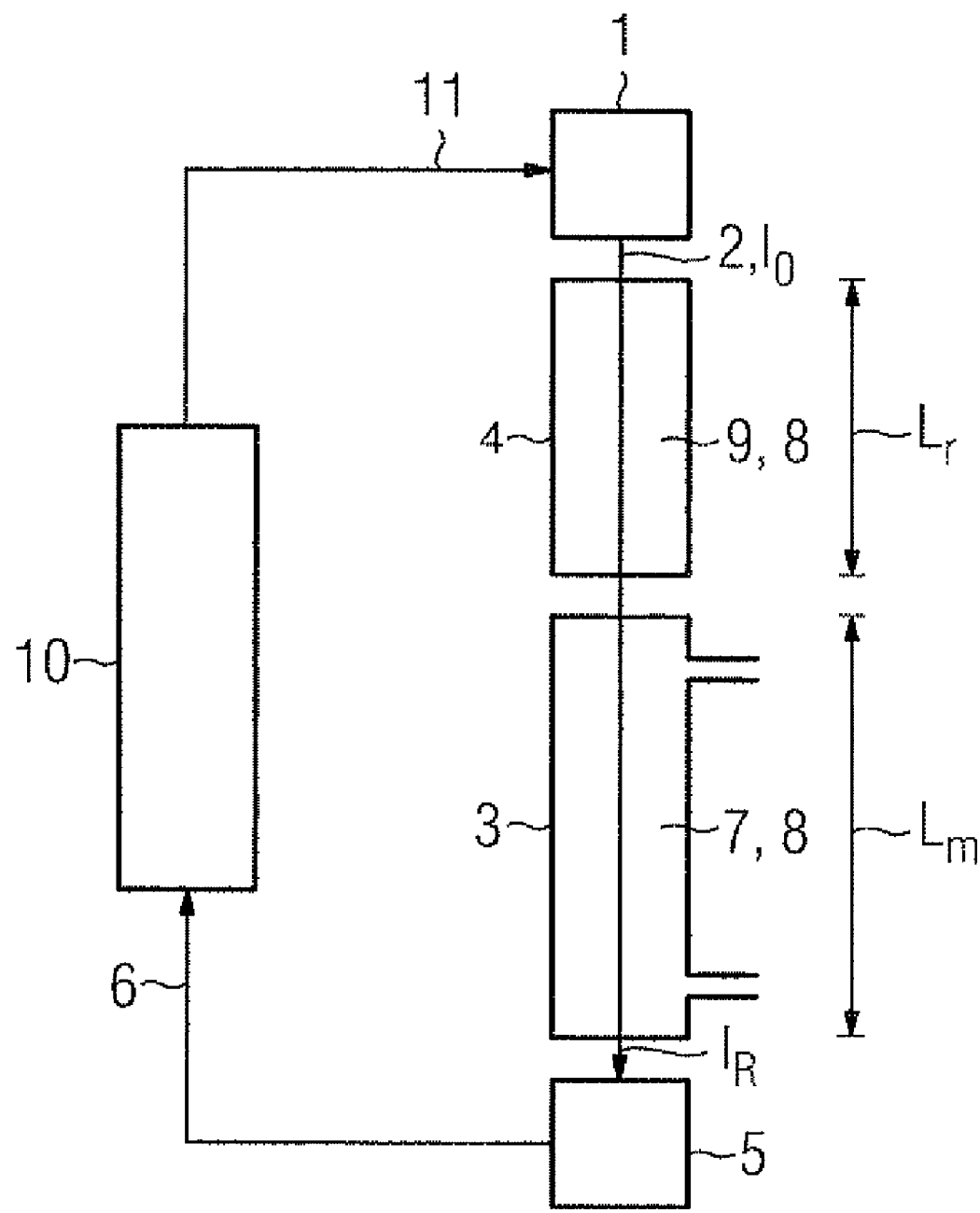
FIG. 1 is a schematic diagram of an apparatus useful for practicing the present invention.

FIG. 1 shows a laser spectrometer as an example for an apparatus for practicing the present invention. The laser spectrometer includes a frequency (wavelength) tunable light source 1 in form of a diode laser for generating light 2 in form of a laser beam which is passed along a single optical path through a measuring volume 3 and a reference cell 4 to a detector 5 for generating a signal 6 indicative of the received light intensity. The measuring volume 3, which can be a sample cell or, in case of in-situ process measurements, a gas-leading pipe, furnace, funnel or the like, contains a measuring gas 7, in which the concentration of a specific gas component 8 is to be measured. The reference gas cell 4 contains a reference gas 9 which comprises the gas component 8 of interest in a known concentration. The signal 6 of the detector 5 is fed to an evaluation and controlling unit 10 for calculating the concentration of the gas component 8 in the measuring gas 7 and for controlling the wavelength tunable light source 1 via a control signal 11.

As the light 2 propagates through weakly absorbing gases, it is attenuated exponentially according to the Beer-Lambert law:

$$I_R = I_0 T \cdot \exp\left[-\sum_i c_i \alpha_i(\nu) L\right], \quad \text{(Equation 1)}$$

where $I_R$ is the intensity of the light 2 received by the detector 5, $I_0$ is the intensity of the light 2 emitted from the light source 1, L is the length of the optical path between the light source 1 and the detector 5, T is a transmission factor including optical losses in the measuring system and in the optical path, $\alpha_i$ is the absorption coefficient of a gas component i with the concentration $c_i$, which absorption coefficient $\alpha_i$ is dependent on the light frequency $\nu$ (or the wavelength). For small optical absorption, Equation 1 reduces to:

$$I_R = I_0 T\left[1 - \sum_i c_i \alpha_i(\nu) L\right]. \quad \text{(Equation 2)}$$

In order to extract the concentration information $c_i$ of a gas component i of interest, the light frequency $\nu$ has to be well determined, i.e. frequency lock is required, as well as the received background light intensity $I_0 T$ has to be known, i.e. normalization of the detector signal 6 is necessary.

In the optical setup of the present invention the reference cell 4 is placed in-line with the measuring volume 3 and filled with a selected isotope of the gas component 8 of interest, wherein the concentration or abundance ratio of said isotope in the reference cell 3 is higher than the known natural-abundance isotope ratio in the measuring volume 4. This provides both the means for locking the tunable light source 1 to the desired frequency (wavelength) and for normalizing the received background light intensity $I_0 T$.

In the following example the concentration of oxygen (as the gas component 8 of interest) in a measuring gas 7 is to be measured. The oxygen molecule has three naturally occurring isotopes: O-16, O-17 and O-18. The most abundant is O-16, with a small percentage of O-18 and an even smaller percentage of O-17. By filling the reference cell 4 with a reference gas 9 comprising the O-18 isotope in a predetermined concentration which is higher than the natural-abundance ratio, a significant absorption line is provided having a well defined wavelength offset from the absorption line of the O-16 isotope. The wavelength of the light 2 of the tunable light source 1 is locked to the absorption line of the O-18 isotope whereas the absorption line of the O-16 isotope is used to measure the oxygen concentration.

Figure 2:
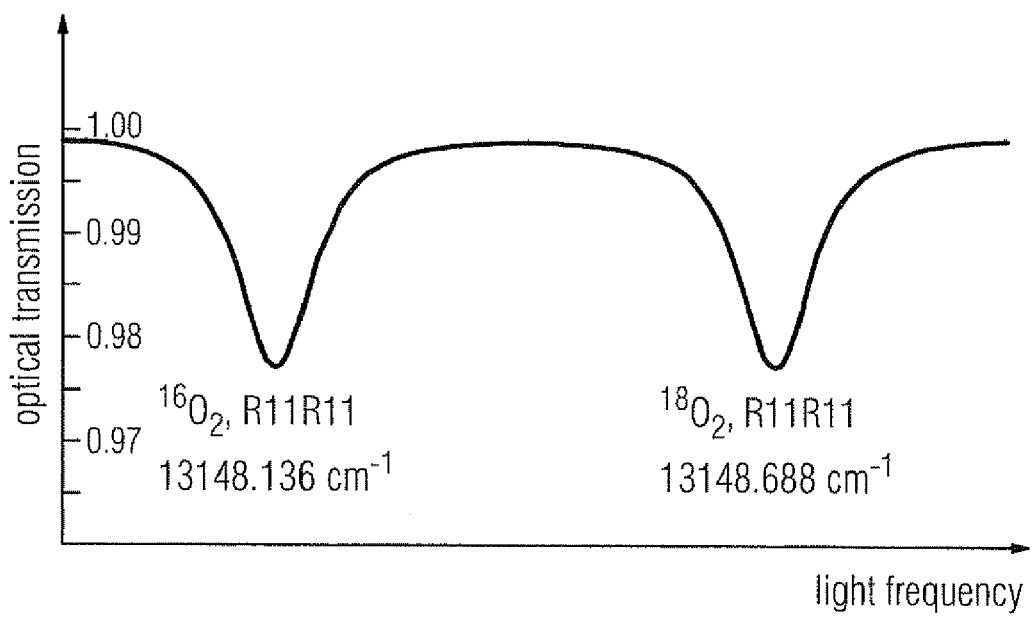
FIG. 2 shows a portion of the absorption spectrum of oxygen as the gas component to be measured.

FIG. 2 shows a portion of the absorption spectrum of oxygen, wherein the isotope $^{18}O_2$ R11R11 line on the right is used for offset-locking of the wavelength of the light 2, while the $^{16}O_2$ R11R11 line is used for the extraction of the oxygen concentration in the measuring volume 3.

Figure 3:
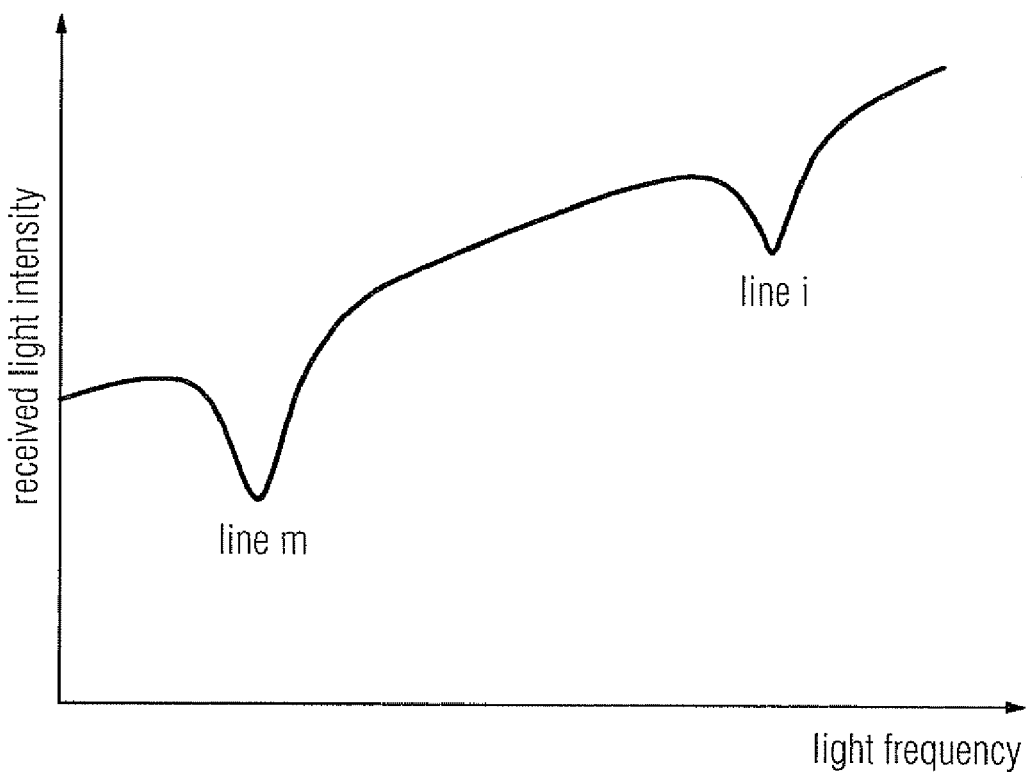
FIG. 3 illustrates the light intensity received in the detector when sweeping the wavelength of the light over the absorption lines of the O-16 and O-18 isotopes.

As FIG. 3 shows, the wavelength of the light 2 is swept by over both the absorption line m of the O-16 isotope in the measuring volume 3 and the absorption line i of the O-18 isotope in the reference cell 4. According to Equation 2, the total received light intensity $I_R$ is equal to a background component $I_0 T$ minus an absorption component. The evaluation and controlling unit 10 extracts from the detector signal 6 the absorption signal component which at the peak of line m is given by:

$$I_m = I_0 T \alpha_m [c_{mm} L_m + c_{mr} \kappa_m(T, p) L_r] \quad \text{(Equation 3)},$$

where $L_m$ is the length of the optical path in the measuring volume 3 (measurement path length), $L_r$ is the length of the optical path in the reference cell 4 (reference path length), $c_{mm}$ is the concentration of the O-16 isotope in the measuring volume 3 and $c_{mr}$ is the concentration of the O-16 isotope in the reference cell 4.

In the same way, the absorption signal component at the peak of line i is given by:

$$I_i = I_0 \eta T \alpha_i [c_{ir} L_r + c_{im} \kappa_i(T,p) L_m] \quad \text{(Equation 4)},$$

where $c_{ir}$ is the concentration of the O-18 isotope in the reference cell 4, $c_{im}$ is the concentration of the O-18 isotope in the measuring volume 3, $\eta = I_0(v_i)/I_0(v_m)$ is the ratio of the emitted light intensities at the center of line i and line m, respectively, and $\kappa(T,p) = \kappa(T) \cdot \kappa(p)$ is a temperature and pressure compensation coefficient correcting for changes in temperature and pressure in the measurement volume 3 relative to the reference cell 4.

The ratio of the peak absorption signal component $I_m$ at line m to the peak absorption signal component $I_i$ at line i yields:

$$R = \frac{I_m}{I_i} = \frac{\alpha_m (c_{mm} L_m + c_{mr} \kappa_m(T,p) L_r)}{\eta \alpha_i (c_{ir} L_r + c_{im} \kappa_i(T,p) L_m)}. \quad \text{(Equation 5)}$$

Since the abundance ratios of the O-18 and O-16 isotopes in the measuring volume $A_m = c_{im}/c_{mm}$ and the reference cell $A_r = c_{ir}/c_{mr}$ are known, Equation 5 can be rewritten as:

$$R = \frac{\alpha_m (c_{mm} L_m + c_{ir} A_r^{-1} \kappa_m(T,p) L_r)}{\alpha_i \eta (c_{ir} L_r + c_{mm} A_m \kappa_i(T,p) L_m)}. \quad \text{(Equation 6)}$$

Thus, the concentration $c_{mm}$ of the O-16 isotope in the measuring volume 3 is given by:

$$c_{mm} = \frac{c_{ir} L_r (R \alpha_i \eta - \alpha_m A_r)}{L_m (\alpha_m \kappa_m(T,p) - A_m R \kappa_i(T,p) \alpha_i \eta)}. \quad \text{(Equation 7)}$$

As the natural-abundance ratio of the O-16 isotope in the measuring volume 4 is known, $c_{mm}$ also defines the concentration of the gas component 8 of interest (here oxygen) in the measuring volume 3.

It is apparent from Equation 7 that the concentration $c_{mm}$ does not depend on the received background light intensity $I_0 T$. Therefore an independent normalization scheme is no longer necessary.

The invention claimed is:

1. A method for measuring a concentration of a gas component in a measuring volume of a measuring gas, comprising:
    providing, in a reference cell, a gas component in a known concentration, the gas component in the reference cell being selected to contain a selected isotope in a known abundance ratio higher than a known natural-abundance isotope ratio of the same gas component;
    passing a light of a wavelength tunable light source along a single optical path through the measuring volume and the reference cell to a detector;
    when passing the light through the measuring volume and the reference cell, tuning the light source to sweep the wavelength of the light over an absorption line of the selected isotope and another absorption line of the remaining gas component;
    generating a signal by the detector, wherein the signal is indicative of the wavelength dependent absorption of the light; and
    calculating the concentration of the gas component in the measuring volume from a ratio of the detector signals at peaks of the absorption lines, based on Lambert's law, wherein the calculation is based upon the known abundance isotope ratios.

2. The method as claimed in claim 1, wherein when the measuring the concentration is oxygen, a O-18 isotope is used as the selected isotope in the reference cell and the detector signals obtained at the peaks of the absorption lines of the O-18 and O-16 isotopes are used for calculating the oxygen concentration.

3. A method for measuring a concentration of a gas component in a measuring gas, comprising:
    selecting and providing a gas component of a reference cell to contain a selected isotope in a known abundance ratio higher than a known natural-abundance isotope ratio of the same gas component in a measuring volume containing a measuring gas;
    passing a light of a wavelength tunable light source along a single optical path through the measuring volume and the reference cell to a detector;
    generating signals by the detector, wherein a first signal is indicative of a wavelength dependent absorption line of the selected isotope in the reference cell and a second signal is indicative of a wavelength dependent absorption line of the selected isotope in the measuring volume, wherein the reference gas comprises the gas component in a known concentration;
    tuning the light source to sweep the wavelength of the light over the absorption lines of the selected isotope and a remaining gas component; and
    calculating the concentration of the gas component in the measuring volume from a ratio of the detector signals at peaks of absorption lines, based on Lambert's law, wherein the calculation is based upon the known abundance isotope ratios.

4. The method as claimed in claim 3, wherein the ratio of the first signal to the second signal is determined.

5. The method as claimed in claim 2, wherein when the measuring concentration is oxygen, a O-18 isotope is used as the selected isotope in the reference cell and the detector signals obtained at the peaks of the absorption lines of the O-18 and O-16 isotopes are used for calculating the oxygen concentration.

* * * * *